US010178947B2

(12) United States Patent
McGrath

(10) Patent No.: US 10,178,947 B2
(45) Date of Patent: Jan. 15, 2019

(54) LARYNGOSCOPE WITH CAMERA ATTACHMENT

(71) Applicant: Aircraft Medical Limited, Edinburgh (GB)

(72) Inventor: Matthew J. R. McGrath, Edinburgh (GB)

(73) Assignee: AIRCRAFT MEDICAL LIMITED, Edinburgh (GB)

( * ) Notice: Subject to any disclaimer, the term of this patent is extended or adjusted under 35 U.S.C. 154(b) by 0 days.

(21) Appl. No.: 15/649,514

(22) Filed: Jul. 13, 2017

(65) Prior Publication Data

US 2017/0303778 A1 Oct. 26, 2017

Related U.S. Application Data

(63) Continuation of application No. 15/209,349, filed on Jul. 13, 2016, now Pat. No. 9,737,202, which is a
(Continued)

(30) Foreign Application Priority Data

Apr. 29, 2003 (GB) .................................. 0309754.0

(51) Int. Cl.
*A61B 1/00* (2006.01)
*A61B 1/267* (2006.01)
(Continued)

(52) U.S. Cl.
CPC .......... *A61B 1/267* (2013.01); *A61B 1/00016* (2013.01); *A61B 1/00052* (2013.01); *A61B 1/00087* (2013.01); *A61B 1/00101* (2013.01); *A61B 1/04* (2013.01); *A61B 1/0661* (2013.01); *A61M 16/0488* (2013.01); *A61N 5/1043* (2013.01); *H05K 999/99* (2013.01); *A61B 1/00029* (2013.01); *A61B 1/00059* (2013.01);
(Continued)

(58) Field of Classification Search
CPC ..... A61B 1/267; A61B 1/2673; A61B 1/2676; A61B 1/00096; A61B 1/00142; A61B 1/00101
See application file for complete search history.

(56) References Cited

U.S. PATENT DOCUMENTS 3,426,749 A * 2/1969 Jephcott ............ A61B 1/00142
206/363
3,643,654 A 2/1972 Felbarg
(Continued)

FOREIGN PATENT DOCUMENTS

EP 653180 A1 5/1995
EP 901772 A1 3/1999
(Continued)

OTHER PUBLICATIONS

Jephcott, The Macintosh laryngoscope, Anaesthesia, 1984, vol. 39, pp. 474-479.
(Continued)

*Primary Examiner* — Timothy J Neal
(74) *Attorney, Agent, or Firm* — Fletcher Yoder PC

(57) ABSTRACT

The invention relates to medical devices for carrying out internal examination, such as laryngoscopes. The laryngoscope is provided with a camera element within a channel inside the blade.

21 Claims, 2 Drawing Sheets

Related U.S. Application Data continuation of application No. 10/554,812, filed as application No. PCT/GB2004/001869 on Apr. 29, 2004, now Pat. No. 9,820,641.

(51) Int. Cl.
*A61N 5/10* (2006.01)
*A61B 1/04* (2006.01)
*A61B 1/06* (2006.01)
*A61M 16/04* (2006.01)
*A61B 90/00* (2016.01)

(52) U.S. Cl.
CPC ... *A61B 1/00062* (2013.01); *A61B 2090/0803* (2016.02); *A61B 2090/0814* (2016.02); *A61B 2560/0276* (2013.01)

(56) References Cited

U.S. PATENT DOCUMENTS

| | | |
|---|---|---|
| 4,086,919 A | 5/1978 | Bullard et al. |
| 4,113,137 A | 9/1978 | Wind et al. |
| 4,306,547 A | 12/1981 | Lowell |
| 4,384,570 A | 5/1983 | Roberts |
| 4,406,280 A | 9/1983 | Upsher et al. |
| 4,556,052 A | 12/1985 | Mueller et al. |
| 4,565,187 A * | 1/1986 | Soloway ............ A61B 1/267 600/193 |
| 4,573,451 A | 3/1986 | Bauman |
| 4,579,108 A | 4/1986 | Bauman |
| 4,742,819 A * | 5/1988 | George ............ A61B 1/00052 348/73 |
| 4,832,003 A | 5/1989 | Yabe et al. |
| 4,832,020 A | 5/1989 | Augustine et al. |
| 4,834,077 A | 5/1989 | Sun et al. |
| 4,934,773 A | 6/1990 | Becker et al. |
| 4,979,499 A | 12/1990 | Sun et al. |
| 4,982,729 A | 1/1991 | Wu et al. |
| 5,003,963 A | 4/1991 | Bullard et al. |
| 5,203,320 A | 4/1993 | Augustine et al. |
| 5,233,426 A | 8/1993 | Suzuki et al. |
| 5,239,983 A | 8/1993 | Katsurada et al. |
| 5,261,392 A | 11/1993 | Wu |
| 5,339,805 A | 8/1994 | Parker et al. |
| 5,349,943 A | 9/1994 | Ruiz |
| 5,363,838 A | 11/1994 | George |
| 5,373,317 A | 12/1994 | Salvati et al. |
| 5,381,787 A | 1/1995 | Bullard et al. |
| D358,471 S | 5/1995 | Cope et al. |
| 5,413,092 A | 5/1995 | Williams et al. |
| 5,443,058 A | 8/1995 | Ough et al. |
| 5,513,627 A | 5/1996 | Flam et al. |
| 5,551,946 A | 9/1996 | Bullard et al. |
| 5,594,497 A | 1/1997 | Ahern et al. |
| 5,645,519 A | 7/1997 | Lee et al. |
| 5,676,635 A | 10/1997 | Levin et al. |
| 5,701,904 A | 12/1997 | Simmons et al. |
| 5,702,351 A | 12/1997 | Bar-Or et al. |
| 5,734,418 A | 3/1998 | Danna |
| 5,734,718 A | 3/1998 | Prafullchandra et al. |
| 5,743,849 A | 4/1998 | Rice et al. |
| 5,754,313 A | 5/1998 | Pelchy et al. |
| 5,762,605 A | 6/1998 | Cane et al. |
| 5,800,342 A | 9/1998 | Lee et al. |
| 5,800,344 A | 9/1998 | Wood et al. |
| 5,827,178 A | 10/1998 | Berall |
| 5,827,428 A | 10/1998 | Chang et al. |
| 5,846,186 A | 12/1998 | Upsher |
| 5,873,818 A | 2/1999 | Rothfels et al. |
| 5,879,289 A | 3/1999 | Yarush et al. |
| 5,879,304 A | 3/1999 | Shuchman et al. |
| 5,895,350 A | 4/1999 | Koichiro et al. |
| 6,080,101 A | 6/2000 | Yutaka et al. |
| 6,083,151 A | 7/2000 | Renner et al. |
| 6,095,972 A | 8/2000 | Sakamoto |
| 6,123,666 A | 9/2000 | Wrenn et al. |
| 6,354,993 B1 | 3/2002 | Kaplan et al. |
| 6,447,444 B1 | 9/2002 | Avni et al. |
| 6,543,447 B2 | 4/2003 | Pacey |
| 6,652,453 B2 | 11/2003 | Smith et al. |
| 6,847,490 B1 | 1/2005 | Nordstrom et al. |
| 7,156,091 B2 | 1/2007 | Koyama et al. |
| 7,182,728 B2 | 2/2007 | Cubb et al. |
| 7,448,377 B2 | 11/2008 | Koyama et al. |
| 8,543,447 B2 | 9/2013 | Corneil et al. |
| 2001/0014768 A1 | 8/2001 | Kaplan et al. |
| 2001/0023312 A1 | 9/2001 | Pacey |
| 2001/0051766 A1 | 12/2001 | Gazdzinski |
| 2002/0022769 A1 | 2/2002 | Smith et al. |
| 2002/0038075 A1 | 3/2002 | Tsai |
| 2002/0087050 A1 | 7/2002 | Rudischhauser et al. |
| 2004/0019256 A1 * | 1/2004 | Cubb ............ A61B 1/267 600/188 |
| 2004/0127770 A1 | 7/2004 | McGrath |
| 2005/0090712 A1 | 4/2005 | Cubb |
| 2006/0276694 A1 | 12/2006 | Gandarias |

FOREIGN PATENT DOCUMENTS

| | | |
|---|---|---|
| EP | 1062905 A1 | 12/2000 |
| EP | 1188420 A1 | 3/2002 |
| EP | 1285623 A1 | 2/2003 |
| FR | 2830428 A1 | 4/2003 |
| GB | 2086732 A | 5/1982 |
| JP | 61141342 A | 6/1986 |
| JP | 2000175867 A | 6/2000 |
| WO | 8301373 A1 | 4/1983 |
| WO | 8911305 A1 | 11/1989 |
| WO | 9104703 A1 | 4/1991 |
| WO | 9819589 A1 | 5/1998 |
| WO | 9841137 A1 | 9/1998 |
| WO | 9927840 A1 | 6/1999 |
| WO | 9944490 A1 | 9/1999 |
| WO | 110293 A1 | 2/2001 |
| WO | 178582 A1 | 10/2001 |
| WO | 178583 A1 | 10/2001 |
| WO | 211608 A2 | 2/2002 |
| WO | 2002007170 | 3/2002 |
| WO | 2056756 A2 | 7/2002 |
| WO | 2095675 A1 | 11/2002 |
| WO | 59366 A2 | 2/2003 |
| WO | 3015619 A1 | 2/2003 |
| WO | 3077738 A1 | 9/2003 |

OTHER PUBLICATIONS

Phscyrembel Klinisches Worterbuch, 1985, pp. 802-803.
Opposition to EP1638451, submission No. 3535510, Jun. 1, 2015.
Opposition to EP1638451, submission No. 3541942, Jun. 3, 2015.
Filing dated Nov. 23, 2015 in Opposition against European Patent No. 1638451B.
Murphy, et al. "Rigid and Semirigid Fiberoptic Intubation", Manual of Emergency Airway Management, The Airways, Lippincott Williams & Wilkins, 2004.
Crosby, et al., "The Unanticipated Difficult Airway with Recommendations for Management", Can J Anaesth 1998 pp. 757-776.
Biro, et al., "Comparison of Two Video-Assisted Techniques for the Difficult Intubation", 2001, pp. 761-765.
Bellhouse, et al., "An Angulated Laryngoscope for Routine and Difficult Trachael Intubation", 1997, pp. 126-129.
Pearce, et al., "Evaluation of the Upsherscope", 1996, pp. 561-564.
Smith, et al., The Complexity of Trachael Intubation Using Rigid Fiberoptic Laryngoscopy (WuScope), Anesth Analg, 1999, pp. 236-239.
Cooper, "Use of a New Videolaryngoscope (GlideScopea) in the Management of a Difficult Airway", Can J Anesth, 2003, pp. 611-613.
Dullenkopf, et al., "Video-enhanced Visualization of he Larynx and intubation with teh Bullard Laryngoscope-equipment report" Can J Anesth 2003, pp. 507-510.

(56) References Cited

OTHER PUBLICATIONS

Thompson, "A New Video Laryngoscope", Anaesthesia, 2004, pp. 410.
Esler, et al., "Decontaminationoflaryngoscopes: asurveyofnational Practice", Anaesthesia, 1999, pp. 582-598.
Morrell, et al., "A Survey of Laryngoscope Contamination at a University and a Community Hospital", Anesthesiology, 1994, pp. 960.
Weiss, M. "Video-intuboscopy: a new aid to routine and difficult tracheal intubation", British Journal of Anaesthesia 1998; 80: 525-527.
Office Action in corresponding JP Application No. 2006-506206 with English translation.
Australian Search Report.
International Search Report.
U.S. Appl. No. 60/067,205, filed Dec. 1, 1997.
U.S. Appl. No. 60/074,355, filed Feb. 10, 1998.
U.S. Appl. No. 60/223,330, filed Aug. 7, 2000.
U.S. Appl. No. 09/060,891, filed Apr. 15, 1998.
U.S. Appl. No. 09/732,129, filed Dec. 6, 2000.
Application No. CH-19980520/98.
Application No. CH-19980523/93.
Application No. CH-19980521/98.
Woodson, "Retropalatal Airway Characteristis in Uvolopalatopharyngoplasty Compared With Transpalatal Advacement Pharyngoplasty"; Laryngoscope 107, Jun. 1997, pp. 735-740.
Satava, "A technologic framework for the future", Surgical Endoscopy (1993) 7:111-113.
Meinke, et al. "What is the learning curve for laparoscopic appendectomy?"; Surgical Endoscopy (1994) 8: 371-375.
Cunningham, "Laparoscopic surger-anesthetic implications"; Surgical Endoscopy (1994) 8: 1272-1284.
Siker ES, "A Mirror Laryngoscope", Anaesthesiology 17:38-42, 1956.

* cited by examiner

LARYNGOSCOPE WITH CAMERA ATTACHMENT

CROSS-REFERENCE TO RELATED APPLICATIONS

This application is a continuation of prior application Ser. No. 15/209,349, filed Jul. 13, 2016, which is a continuation of prior application Ser. No. 10/554,812, filed Nov. 30, 2006, which is the National Stage of International Application No. PCT/GB04/01869, filed Apr. 29, 2004, which claims priority to United Kingdom Patent Application No. 0309754.0, filed Apr. 29, 2003.

BACKGROUND OF THE INVENTION

The present invention relates to medical devices for carrying out internal examination and relates particularly to laryngoscopes that incorporate image capturing means such as a camera to assist intubation of a tracheal tube.

Insertion of a tracheal tube is an important procedure in providing an airway to an anaesthetist prior to a surgical operation. Tracheal tubes also often need to be inserted in an emergency situation into the airway of an unconscious patient by paramedics or doctors. Insertion of a tracheal tube requires significant skill, and laryngoscopes are generally used to assist the insertion of the tube by restraining the patient's tongue and allowing a clear view of the larynx and the entrance to the trachea. Considerable skill and care is required in carrying out this procedure in order to avoid damage to the patient's teeth and soft tissue of the throat.

Often problems occur when a practitioner is attempting to intubate a patient using a laryngoscope as it can be difficult for the practitioner to see what is going on.

Figures show that in approximately 12% of cases trauma occurs during intubation (which affects a large number of people when you consider there are over 40 million intubations carried out annually). Also, during the 1980s and 1990s, 2500 deaths (or approximately 3 per week) occurred in Europe due to an inability to intubate and these figures have not changed substantially in recent years. Airway problems remain the most frequent cause of death or permanent brain damage associated with anaesthesia.

Generally, laryngoscopes consist of a handle, or body, portion and a blade portion. Certain devices have been developed which incorporate a camera element attached to the blade. However, this has led to issues relating to the cleaning of the laryngoscope before re-use. Obviously in order to use a laryngoscope on a patient, it is important to know that the laryngoscope is cleaned sufficiently and there is no risk of cross contamination between patients. There is evidence to show that standard cleaning procedures are not always fully effective at removing contaminants such as bacteria from the laryngoscope (J R Hall. "Blood contamination of equipment . . . " Anaesthesia and Analgesia. 1994; 78:1136-9 M D Ester, L C Baines, D J Wilkinson & R M Langford. "Decontamination of Laryngoscopes: a survey of national practice." Anaesthesia, 1999, 54).

Typically, to clean a laryngoscope, the blade is soaked and autoclaved. The handle can undergo a similar procedure or can simply be wiped down as it does not make contact with the patient as the blade does. The cleaning takes a significant amount of time, which means that it is necessary to have a number of handles and blades in rotation to ensure that there are always clean laryngoscopes available if required. This results in a time consuming and costly procedure needing to be put in place. Obviously the cleaning procedure is significantly more difficult when there is also a camera element that requires cleaning and this can cause significant delays and a cost implication. This means that laryngoscopes incorporating camera elements are rarely used in practice.

In order to try and overcome the issues associated with the use of laryngoscopes and similar medical devices, a number of alternative device products have been suggested or developed. For example, disposable blades are available for use, however, these can be lacking in strength and only allow the most basic airway opening to be achieved due to their relative simplicity of design. Protective sheaths can also be used which slip over a standard laryngoscope blade to act as a guard. While useful, it is optional to a user whether the sheath is used or not. For the user, existing blades perform better without the sheath, which distorts light output and, as a result, existing sheaths are rarely used.

Preferred embodiments of the present invention seek to improve upon the products described in the prior art.

Throughout this Application the term blade should be read in a broad sense to cover not only laryngoscope blades but also to cover speculums or elements that are inserted into body cavities.

SUMMARY OF THE INVENTION

According to a first aspect of the present invention, there is provided a medical device for carrying out internal examination, comprising a body portion and a blade portion, characterised in that the blade portion comprises an at least partially rigid probe means which is at least partially transparent and through which a channel partially runs and wherein an image capture means is provided within the channel. In an alternative embodiment there may be a light source provided in the channel. This may be associated with the camera element if desired.

In this instance, rigid should be construed as providing sufficient structural integrity to hold its own form under normal conditions. For example, as well as materials such as plastics and metals, rubber materials that are able to hold their own shape, but have some resistance if compressed, i.e., dropped or stood on.

Optionally, the entire rigid probe means is transparent.

Preferably, at least part of the transparent section of the rigid probe means forms a lens for use with the image capture means.

Optionally, lenses can be used to transfer image and/or light through a curved or angled portion of the blade.

Optionally, reflecting means can be used to transfer image and/or light through a curved or angled portion of the blade.

Preferably the rigid probe means has a spatulate shape.

Preferably the image capture means is a camera.

Optionally the image capture means is a fibre optic cable that is able to transmit an image.

Preferably, the medical device for carrying out internal examination is a laryngoscope.

Preferably a light source is provided in the channel.

Optionally, a strengthening element is provided in the channel.

Preferably the strengthening element is in the form of a steel rod which could have any appropriate cross-section.

Preferably the body section is provided with a screen for showing the images captured by the image capturing means and any other information.

Preferably data and power is transferred between the body element and the blade element wirelessly.

Preferably data and power is transferred between the body element and the blade element via contact points present on both the body element and the blade element.

Alternatively data is transferred between the body element and the blade element by optical transfer means.

Alternatively data is transferred between the body element and the blade element by radio frequency transfer means.

According to a second aspect of the present invention, there is provided a rigid probe means for use with medical devices for internal examination, characterised in that the rigid probe means is at least partially transparent and has a channel running partially through it.

Preferably the channel runs-in a longitudinal direction.

Optionally, the entire rigid probe means is transparent.

Preferably, at least part of the rigid probe means forms a lens.

Preferably the rigid probe means has a spatulate shape.

BRIEF DESCRIPTION OF THE DRAWINGS

In order to provide a better understanding of the present invention, embodiments will now be described by way of example only, and with reference to the following Figures, in which.

DETAILED DESCRIPTION

In the preferred embodiment of the present invention, the medical device is a laryngoscope which can be used for intubation of a tracheal tube.

Figure 1:
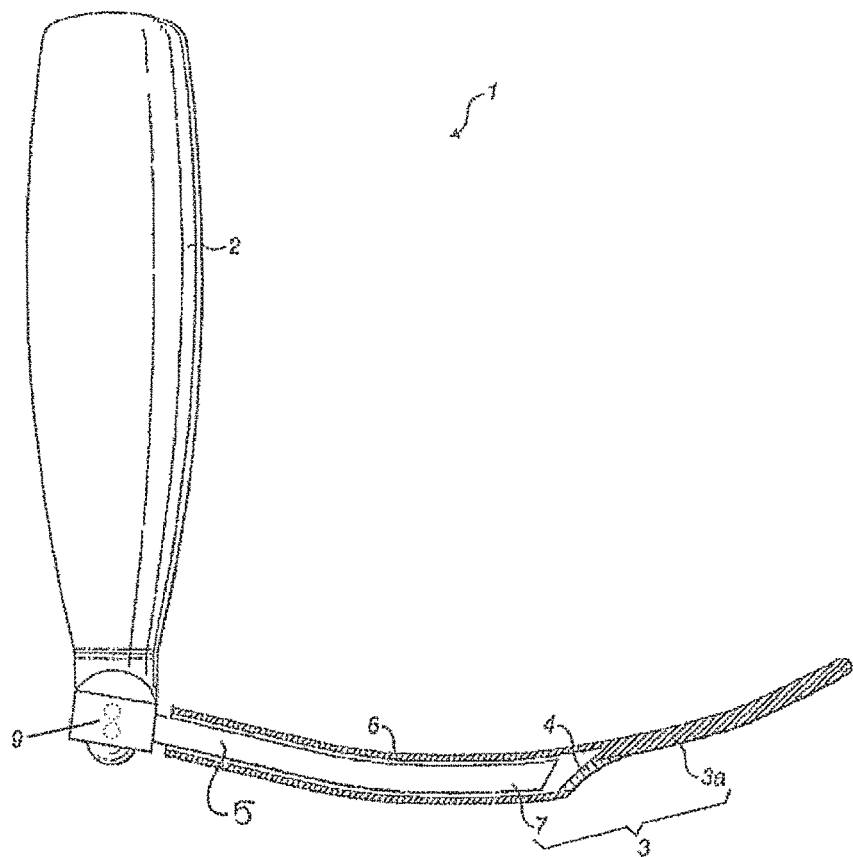
FIG. 1 shows a drawing of a laryngoscope according to one embodiment of the present invention.

A laryngoscope 1 is provided which has a body 2 and a disposable blade 3. In the preferred embodiment, as shown in FIG. 1, the blade 3 is made up from a rigid probe means 3a that has a spatulate shape. The rigid probe means 3a has an internal channel 6 which has a camera element 7 inserted into it, such that the camera element 7 does not come into contact with the patient. The camera element 7 is elongate in form, and has any appropriate cross-section. The end of the camera element 7 that is not inserted into the channel 6 attaches to the body section 2. As the rigid probe means 3a fits over the camera element 7 like a sleeve, the camera element 7 will not come into contact with the patient during examination. This means that the camera element 7 that has been inserted into the channel 6 can be re-used while the rigid probe means 3a, which forms the outer layer, can be discarded. The body 23 is provided with a screen 10 for showing the images captured by the camera element 7 and other information.

Figure 2:
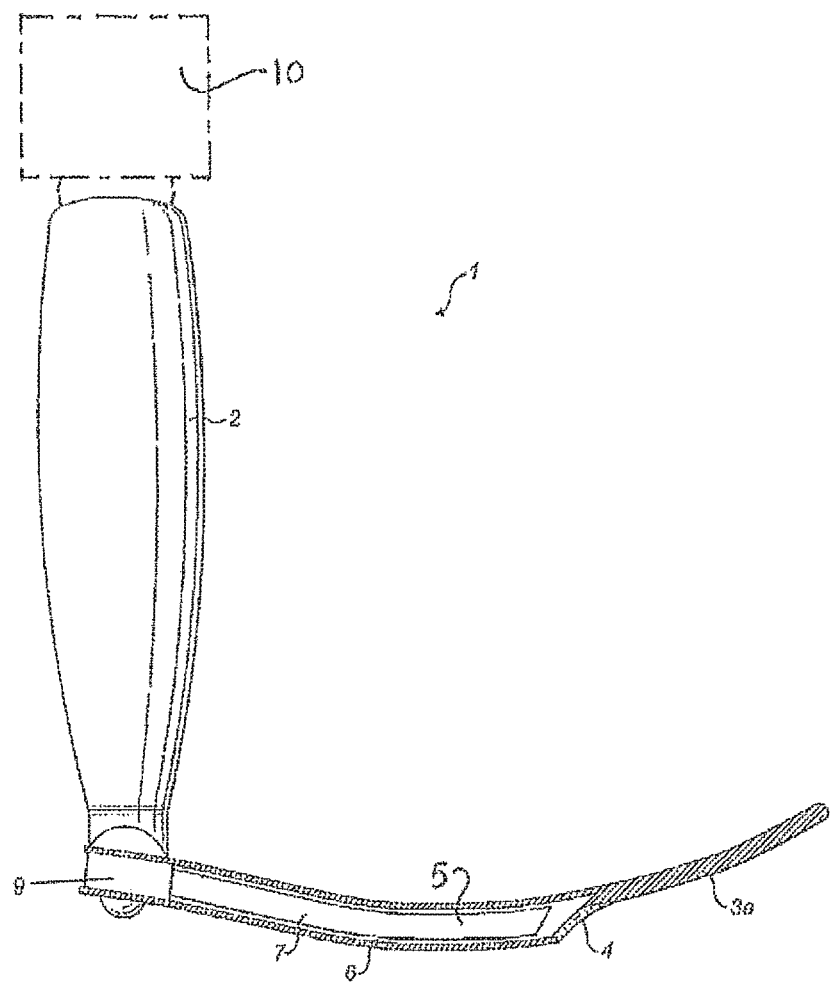
FIG. 2 shows a drawing of a laryngoscope according to another embodiment of the present invention.

In an alternative embodiment, as shown in FIG. 2, the rigid probe means 3a covers more of the length of the camera element 7 and attaches to the body section 2 of the laryngoscope 1 directly.

In the preferred embodiment, the rigid probe means 3a is made from a transparent material, such as plastic or perspex. If additional strength is required, a strengthening element 5 can be inserted into the channel 6 within the rigid probe means 3a, either as an integral element which can be discarded along with the rigid probe means 3a after use, or as a reusable element which can optionally be attached to the body 2 of the laryngoscope 1, such that it can be inserted into the next rigid probe means 3a that is to be used.

The laryngoscope 1 may have a screen 10, shown in dashed lines in FIG. 2, for showing the images captured by the camera element 7 and any other information. The screen 10 may couple to the body section 2.

The channel 6 can also be used to house a light source, which can be inserted into the channel 6 in the centre of the rigid probe means 3a so that a practitioner can visualise a trachea to help in the positioning of a tracheal tube. The electrical components which run the camera element 7 or the light can be housed in the body 2 of the laryngoscope 1 or externally to the laryngoscope 1 and the relevant parts can simply be slipped in and out of the channel 6 and of the blade 3 when required. This again means that the blade 3 can be discarded with the expensive lighting or camera elements 7 being kept for further use, without them having ever been in contact with a patient.

In order to allow the blade 3 and body 2 to be easily separable, data is transferred wirelessly between the camera element 7 and the body 2, which contains electrical components that relate to the camera element 7. The wireless transfer is preferably via contact points in the form of contact strips 8 but can also be via optical data transfer methods or radio frequency data transfer methods. This use of wireless data transfer removes the need for a flying lead between the body 2 and blade 3 which make cleaning more difficult and can result in the laryngoscope 1 being clumsy to use.

Figure 3:
FIG. 3 shows a drawing of the contact strips according to an embodiment of the present invention.

The contact points are preferably in the form of conductive contact strips 8. In the preferred embodiment the strips 8 are formed partially on the camera element 7 and partially on the rigid probe means 3a such that when the camera element 7 is inserted into the rigid probe means 3a, the strips 8a and 8b are brought into contact to form continuous strips 8. In typical cases, there will be four contact strips 8, two for transferring data and two for transferring power (FIG. 3). The body 2 containing electrical components which run the camera element 7 is also provided with contact points and these will usually be in the form of retractable bearings 9 or retractable pins or other resiliently biased contact means.

These bearings or pins may also act as a gripping method to hold the blade 3 in place. Corresponding ratchet type tracks (preferably conductive) enables the blade 3 to be adjusted in length.

In order to miniaturise a camera element 7, at least part of the transparent section of the rigid probe means 3a forms a lens 4, such that the camera element 7 itself does not require a lens, but can simply be slipped into the channel 6 of the blade 3. The lens 4 on the blade 3 acts then acts as a lens 4 for the camera element 7. This inclusion of the lens 4 into the disposable rigid probe means 3a means that the camera element 7 can be smaller than is typically achievable, making it particularly suitable for use in a medical device, such as a laryngoscope 1.

One of the benefits of the disposability of the rigid probe means 3a part of the blade 3 is that there will be no cross-contamination to patients, and no lengthy cleaning procedures are required. However, to further ensure that a blade 3 is not reused, it is possible to include a spoiling mechanism between the blade 3 and the body 2 of the laryngoscope 1. The spoiling mechanism can take the form of a breaking of electrical connections when the blade 3 and body 2 are parted, such that if the same blade 3 and body 2 are reconnected, no power is provided to anything inserted into the channel 6 of the blade 3. Alternatively, the blade 3 may comprise protrusions which are able to fix into ingressions in the body 2 of the laryngoscope 1, such that the protrusions break off when the blade 3 is removed from the body 2, such that the blade 3 cannot then be reused.

It can be seen that the current invention has a number of benefits over the prior art and a number of possible uses. Although the examples above relate to a laryngoscope, it can be seen that the concept can be extended to other medical and veterinary devices and still stay within the scope of the present invention. The fact that the blade 3 is fully disposable is also of great importance, as it means that practitioners are required to change blades and the product is both simple to use and cheap to manufacture.

It will be appreciated by persons skilled in the art that the above embodiment has been described by way of example only, and not in any limiting sense, and that various alterations and modifications are possible without departure from the scope of the invention as defined by the appended Claims.

What is claimed is:

1. A laryngoscope blade configured to be used in conjunction with a laryngoscope handle portion to assist intubation of a patient, comprising:
    a blade body comprising:
        a sleeve forming a channel between at least two opposing outer walls, the channel running in a longitudinal direction and terminating in a closed end face, wherein the closed end face is transparent, each outer wall having a wall thickness as measured orthogonal to the longitudinal direction; and
        a rigid spatulate shaped portion that extends in the longitudinal direction past the closed end face of the channel by a distance that is greater than a dimension of the channel as measured orthogonal to the longitudinal direction, and wherein the rigid spatulate shaped portion is thicker than the wall thickness along an entire length of the rigid spatulate shaped portion.

2. The laryngoscope blade of claim 1, comprising a mating feature configured to accommodate a pin or bearing of the laryngoscope handle portion.

3. The laryngoscope blade of claim 1, wherein the channel is curved.

4. The laryngoscope blade of claim 1, wherein the rigid spatulate shaped portion is elongated in the longitudinal direction past the closed end face.

5. The laryngoscope blade of claim 1, wherein a strengthening element is provided in the channel.

6. The laryngoscope blade of claim 5, wherein the strengthening element is reusable and insertable into another laryngoscope blade.

7. The laryngoscope blade of claim 1, wherein the strengthening element is integral with the blade body.

8. The laryngoscope blade of claim 1, wherein the laryngoscope blade is entirely transparent.

9. The laryngoscope blade of claim 1, wherein the proximal opening of the channel is shaped to accommodate a rod.

10. A laryngoscope blade configured to be used in conjunction with a laryngoscope handle portion to assist intubation of a patient, comprising:
    an outer wall forming a channel, the channel extending from a proximal opening and terminating in a closed end face partway along the blade, wherein the closed end face is transparent; and
    a rigid spatulate shaped portion that extends past the closed end face of the channel and terminating at a distal end of the laryngoscope blade, wherein the rigid spatulate shaped portion is elongated in a longitudinal direction past the closed end face, and wherein the rigid spatulate shaped portion is thicker than the outer wall along an entire length of the rigid spatulate shaped portion.

11. The laryngoscope blade of claim 10, comprising a camera element positioned within the channel.

12. The laryngoscope blade of claim 11, wherein a strengthening element is provided in the channel.

13. The laryngoscope blade of claim 10, wherein a longest dimension across a proximal opening of the channel is approximately equal to a longest dimension across a midpoint of the channel.

14. A laryngoscope blade, configured to be used in conjunction with a laryngoscope handle portion to assist intubation of a patient, comprising:
    a blade body, comprising:
    an outer wall forming a channel, the channel extending from a proximal opening and terminating in a closed end face, wherein the closed end face is transparent and comprises a lens; and
    a rigid spatulate shaped portion that extends in a longitudinal direction past the closed end face of the channel by a distance that is greater than a dimension of the channel as measured orthogonal to the longitudinal direction, and wherein the rigid spatulate shaped portion is thicker than the outer wall along an entire length of the rigid spatulate shaped portion, the thickness being measured orthogonal to the longitudinal direction.

15. The laryngoscope blade of claim 14, wherein the rigid spatulate shaped portion is elongated in the longitudinal direction past the closed end face.

16. The laryngoscope blade of claim 14, wherein the channel is curved.

17. The laryngoscope blade of claim 14, wherein the laryngoscope blade is entirely transparent.

18. The laryngoscope blade of claim 14, wherein the laryngoscope blade is disposable.

19. The laryngoscope blade of claim 14, wherein a strengthening element is provided in the channel.

20. The laryngoscope blade of claim 19, wherein the strengthening element is reusable and insertable into another laryngoscope blade.

21. The laryngoscope blade of claim 14, comprising a strengthening element, wherein the strengthening element is integral with the blade body.

* * * * *